(12) United States Patent
Lieberman (10) Patent No.: US 6,953,462 B2
(45) Date of Patent: Oct. 11, 2005

(54) APPARATUS FOR IMPLANTATION INTO BONE

(75) Inventor: Isador H. Lieberman, Pepper Pike, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 175 days.

(21) Appl. No.: 10/395,779

(22) Filed: Mar. 24, 2003

(65) Prior Publication Data

US 2003/0181913 A1 Sep. 25, 2003

Related U.S. Application Data

(63) Continuation-in-part of application No. 09/708,940, filed on Nov. 8, 2000, now Pat. No. 6,551,322.
(60) Provisional application No. 60/238,271, filed on Oct. 5, 2000.

(51) Int. Cl.[7] ............................................. A61B 17/56
(52) U.S. Cl. .............................. 606/72; 606/61; 606/71
(58) Field of Search .............................. 606/61, 70, 72, 606/73; 411/411, 421

(56) References Cited

U.S. PATENT DOCUMENTS

| | | |
|---|---|---|
| 2,033,039 A | 3/1936 | Limpert |
| 4,762,453 A | 8/1988 | DeCaro |
| 4,854,311 A | 8/1989 | Steffee |

(Continued)

FOREIGN PATENT DOCUMENTS

| | | |
|---|---|---|
| DE | 0374088 A1 | 10/1989 |
| DE | 0663184 A1 | 7/1995 |
| FR | 2299548 | 8/1976 |
| SU | 1071297 A | 2/1984 |
| WO | WO0224087 A1 | 3/2002 |

OTHER PUBLICATIONS

An article entitled "Anterior Vertebral Body Screw Pullout Testing, A Comparison of Zielke, Kaneda, Universal Spine System, and Universal Spine System With Pullout–Resistant Nut", by Isador H. Lieberman, et al., Reprinted from SPINE, vol. 23, No. 8, Apr. 15, 1998.

An excerpt from The Application of Shape Memory Alloys in Medicine; Author: I.P. Lipscomb, 1996; Contents; Forward; Preface; Chapter 1 "Introduction to Shape Memory Alloys (SMAs)".

An excerpt from The Application of Shape Memory Alloys in Medicine; Author: I.P. Lipscomb, 1996; Chapter 2 entitled "Characteristics of Shape Memory Alloys in Medical Applications".

An excerpt from The Application of Shape Memory Alloys in Medicine; Author: I. P. Lipscomb, 1996; Chapter 5 "Present and Future Orthopaedic Applications".

*Primary Examiner*—Eduardo C. Robert
(74) *Attorney, Agent, or Firm*—Tarolli, Sundheim, Covell & Tummino L.L.P.

(57) ABSTRACT

An anchor is implantable into a bone in a patient's body and, when implanted, is resistant to toggling in the bone and to being pulled from the bone. The anchor includes a head end portion having a surface that extends transverse to a central axis of the anchor and is engagable with the bone. A plurality of helical spikes extend from the surface on the head end portion and are engagable with the bone. Each of the plurality of helical spikes has a helical central axis that forms a helix around the central axis of the anchor. Each of the plurality of helical spikes further has a circular cross-sectional configuration as viewed in a plane extending perpendicular to the helical central axis of each of the helical spikes and a distal end portion with a tip that penetrates the bone as the head end portion is rotated relative to the bone.

17 Claims, 9 Drawing Sheets

U.S. PATENT DOCUMENTS

| | | |
|---|---|---|
| 4,961,740 A | 10/1990 | Ray et al. |
| 5,055,104 A | 10/1991 | Ray |
| 5,116,336 A | 5/1992 | Frigg |
| 5,246,443 A | 9/1993 | Mai |
| 5,263,953 A | 11/1993 | Bagby |
| 5,290,289 A | 3/1994 | Sanders et al. |
| 5,437,266 A | 8/1995 | McPherson et al. |
| 5,534,031 A | 7/1996 | Matsuzaki et al. |
| 5,582,616 A | 12/1996 | Bolduc et al. |
| 5,626,613 A | 5/1997 | Schmieding |
| 5,662,683 A | 9/1997 | Kay |
| 5,728,116 A | 3/1998 | Rosenman |
| 5,791,899 A | 8/1998 | Sachdeva et al. |
| 5,800,550 A | 9/1998 | Sertich |
| 5,810,851 A | 9/1998 | Yoon |
| 5,824,008 A | 10/1998 | Bolduc et al. |
| 5,888,223 A | 3/1999 | Bray, Jr. |
| 5,904,696 A | 5/1999 | Rosenman |
| 6,010,502 A | 1/2000 | Bagby |
| 6,036,701 A | 3/2000 | Rosenman |
| 6,071,310 A | 6/2000 | Picha et al. |
| 6,080,155 A | 6/2000 | Michelson |
| 6,102,950 A | 8/2000 | Vaccaro |
| 6,106,557 A | 8/2000 | Robioneck et al. |
| 6,113,638 A | 9/2000 | Williams et al. |
| 6,117,162 A | 9/2000 | Schmieding et al. |
| 6,120,502 A | 9/2000 | Michelson |
| 6,120,503 A | 9/2000 | Michelson |
| 6,123,705 A | 9/2000 | Michelson |
| 6,126,688 A | 10/2000 | McDonnell |
| 6,126,689 A | 10/2000 | Brett |
| 6,139,550 A * | 10/2000 | Michelson .................. 606/69 |
| 6,206,882 B1 | 3/2001 | Cohen |
| 6,296,656 B1 | 10/2001 | Bolduc et al. |
| 6,468,309 B1 | 10/2002 | Lieberman |
| 6,527,774 B2 * | 3/2003 | Lieberman .................. 606/61 |
| 6,551,319 B2 * | 4/2003 | Lieberman .................. 606/61 |
| 6,551,322 B1 * | 4/2003 | Lieberman .................. 606/69 |

* cited by examiner

APPARATUS FOR IMPLANTATION INTO BONE

RELATED APPLICATIONS

This application is a continuation-in-part of U.S. patent application Ser. No. 09/708,940, filed Nov. 8, 2000, now U.S. Pat. No. 6,551,322 which corresponds to U.S. Provisional Patent Application Ser. No. 60/238,271, filed Oct. 5, 2000, and which is assigned to the assignee of the present application.

TECHNICAL FIELD

The present invention is directed to an apparatus for implantation into a bone in a patient's body, and is particularly directed to an apparatus that, when implanted, is resistant to toggling in the bone and to being pulled from the bone.

BACKGROUND OF THE INVENTION

Bone screws are used in the medical field for a variety of purposes. Typical uses for bone screws, also referred as bone anchors, include treating a bone fracture, attaching a corrective device to parts of a fractured bone in an area adjacent to the fracture, and attaching a corrective device to a group of bones, such as vertebrae of a spinal column.

Most known bone screws use a conventional screw design, i.e. a solid shank, with one or more external thread convolutions. The solid shank and external threads of the conventional bone screws can cause the bone screws to displace an undesirably large amount of bone when implanted. It is also known to use a corkscrew-style helical spike as a tissue anchor. The known corkscrew-style tissue anchors, when implanted, displace less bone than the conventional bone screws, but are generally not able to withstand high tensile loads without structural failure. European Patent No. 0 374 088 A1 discloses a bone screw having a twin-corkscrew design. In this twin-corkscrew design, which is formed by drilling a passage up through a screw having a solid shank and then machining out the material between the two corkscrews, the junction of the corkscrews with the shank is unlikely to be capable of structurally withstanding high tensile loads and repetitive fatigue loads. This structural weakness in the design of the screw in the EP 0 374 088 document is further compounded by the corkscrews having a larger overall diameter than the head of the screw where torque is applied.

One of the more challenging applications of a bone screw is implantation of the screw into the cancellous bone of a patient's spine or pelvis. For example, bone screws are frequently implanted into the cancellous bone of a patient's lumbar vertebrae during a spinal fixation procedure to correct scoliosis. Once implanted, the bone screws are used to mount suitable spinal fixation instrumentation, such as clamps, rods, and plates. Unfortunately, many of the known bone screws, such as those described above, can be susceptible to toggling in the vertebral body and can also pull out of the vertebral body due to the substantial forces on the screws from human body movement and muscle memory. In order to achieve a high pull-out resistance, it is known to thread a bone screw all of the way through a vertebrae and place a nut on the opposite side. However, use of such a nut increases the complexity of the surgical procedure.

Hence, it is desirable to provide an apparatus for implantation into a bone in a patient's body in a minimally invasive endoscopic procedure, wherein the apparatus provides a platform for connecting spinal fixation instrumentation and, when implanted, is highly resistant to toggling in the bone and to being pulled out of the bone despite the substantial forces on the apparatus from human body movement and muscle memory.

SUMMARY OF THE INVENTION

The present invention is an anchor which is implantable into a bone in a patient's body and, when implanted, is resistant to toggling in the bone and to being pulled from the bone. The anchor comprises a head end portion having a surface that extends transverse to a central axis of the anchor and is engagable with the bone. A plurality of helical spikes extend from the surface on the head end portion of the anchor and are engagable with the bone. Each of the plurality of helical spikes has a helical central axis that forms a helix around the central axis of the anchor. Each of the plurality of helical spikes further has a circular cross-sectional configuration as viewed in a plane extending perpendicular to the helical central axis of each of the helical spikes and a distal end portion with a tip that penetrates the bone as the head end portion is rotated relative to the bone.

The present invention further provides a method of implanting an anchor in a patient's body. According to the inventive method, a cannula is positioned relative to a bone in a patient's body. An anchor, having a plurality of helical spikes extending from a surface on a head end portion of the anchor, is moved along a path extending through the cannula with pointed end portions of the helical spikes leading and the head end portion trailing. The bone is engaged with the pointed end portions of the helical spikes while moving the anchor along the path extending through the cannula. The anchor is rotated about a central axis of the anchor after engaging the bone with the pointed end portions of the helical spikes. The bone is penetrated with the helical spikes as the anchor is rotated about its central axis. The surface on the head end portion of the anchor is moved into engagement with the bone at a location between the helical spikes.

The present invention further provides an apparatus comprising at least one anchor which is implantable into a bone in a patient's body and, when implanted, is resistant to toggling in the bone and to being pulled from the bone, and a fixation implant for extending between and connecting a plurality of bones. The at least one anchor includes a head end portion having a surface which extends transverse to a central axis of the anchor and is engagable with the bone. The head end portion has means for connecting with the fixation implant. The head end portion of the at least one anchor has a plurality of helical spikes that extend from the surface and which extends transverse to a central axis of the at least one anchor and are engagable with the bone. Each of the plurality of helical spikes has a helical central axis that forms a helix around the central axis of the at least one anchor. Each helical spike of the plurality of helical spikes further has a distal end portion with a tip that penetrates the bone as the at least one anchor is rotated relative to the bone and a circular cross-sectional configuration as viewed in a plane extending perpendicular to the helical central axis of the one helical spike throughout a length of the one helical spike extending from the proximal end portion to the distal end portion of the one helical spike.

BRIEF DESCRIPTION OF THE DRAWINGS

The foregoing and other features of the present invention will become apparent to those skilled in the art to which the present invention relates upon reading the following description with reference to the accompanying drawings, in which.

DESCRIPTION OF EMBODIMENTS

Figure 1:
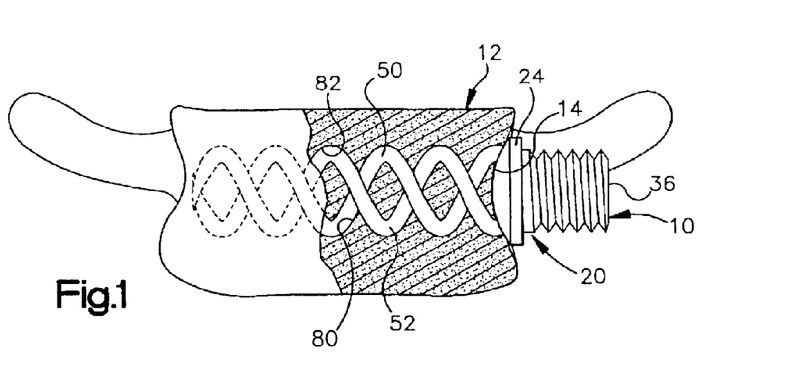
FIG. 1 is a schematic anterior view of an apparatus constructed in accordance with the present invention implanted in a vertebral body.

The present invention is directed to an apparatus for implantation into a bone in a patient's body, and is particularly directed to an apparatus that, when implanted, is resistant to toggling in the bone and to being pulled from the bone. As representative of the present invention, FIG. 1 illustrates an apparatus 10 implanted in a lumbar vertebrae 12. It should be understood that the apparatus 10 could be implanted into any number of different bones in a mammalian body, including but not limited to vertebral bones. The lumbar vertebrae 12 has a concave side surface 14.

Figures 4, 5, 6:
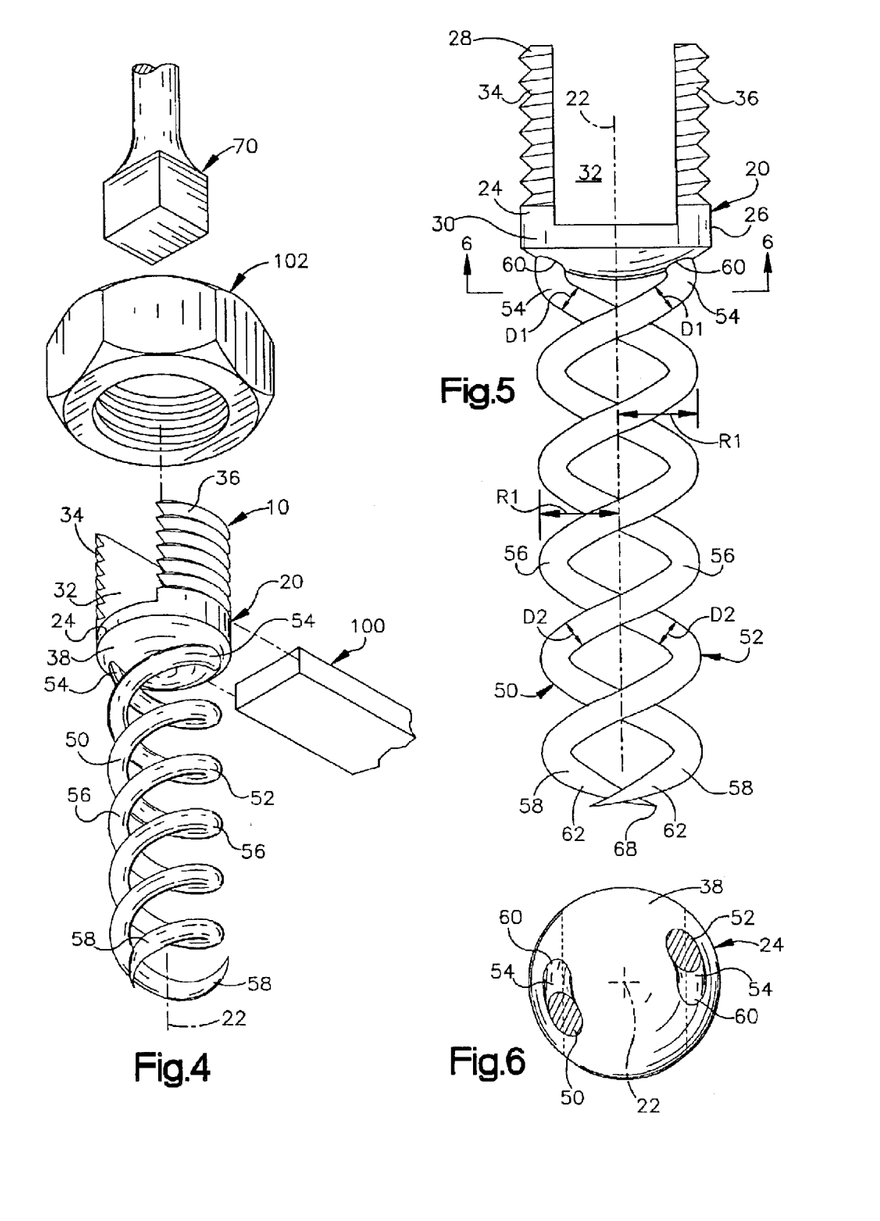
FIG. 4 is an exploded perspective view of the apparatus of FIG. 2, and illustrates a driver for rotating the apparatus.
FIG. 5 is a side view of the apparatus of FIG. 1.
FIG. 6 is a sectional view taken along 6—6 in FIG. 5.
Figure 6A:
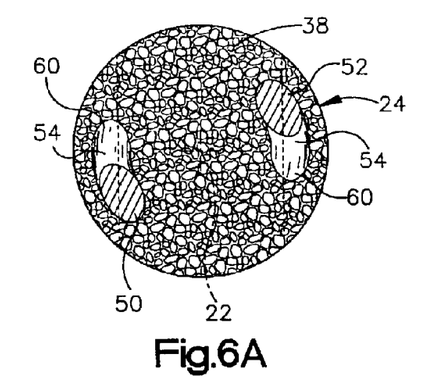
FIG. 6A is a view similar to FIG. 6 illustrating an alternative feature of the invention.

The apparatus 10 comprises an anchor 20 made from a biocompatible material, such as titanium or stainless steel. It is contemplated that the biocompatible material used to make the anchor 20 could also be biodegradable. The anchor 20 is centered about a longitudinal axis 22 (FIG. 5). The anchor 20 includes a platform 24 having a generally cylindrical outer surface 26 extending between oppositely disposed first and second ends 28 and 30 of the platform. The platform 24 includes a generally rectangular slot 32 that extends axially from the first end 28 toward the second end 30 of the platform. Adjacent the first end 28, the outer surface 26 of the platform 24 includes first and second segments of external threads 34 and 36 that are separated by the slot 32. The slot 32 and the threads 34 and 36 provide structure for connecting spinal fixation instrumentation to the platform 24 as discussed further below. The second end 30 of the platform 24 includes an end surface 38 (FIG. 6) having a convex shape that is complimentary to the shape of the concave side surface 14 of the vertebrae 12. It is contemplated that the complimentary shape of the end surface 38 could range from concave to flat to convex depending on the specific shape of the bone surface to be engaged. The end surface 38 of the platform 24 may include barbs (not shown) or other suitable structure for fixedly engaging the side surface 14 of the vertebrae 12. As shown in FIG. 6A, the end surface 38 may have a porous texture, formed by mesh, beads, or a coating such as a ceramic coating, that increases the surface area of the end surface to promote bone in-growth and thus help with long term fixation of the anchor 20 to the bone.

Figure 1A:
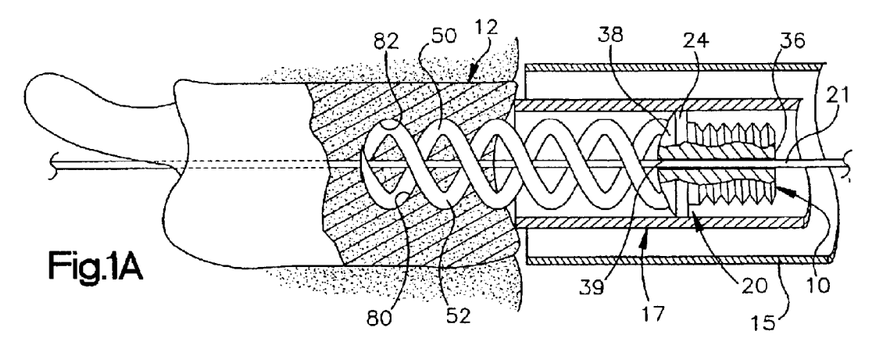
FIG. 1A is view similar to FIG. 1 showing the apparatus partially implanted.

As shown in FIG. 1A, the platform 24 may further include a central bore 39 for receiving a wire (or pin) 21 that has been previously passed through the vertebrae 12 across the anatomically defined trajectory. The wire 21 is used to ensure proper alignment of the anchor 20 during insertion into the vertebrae.

First and second helical spikes 50 and 52 project tangentially from the end surface 38 of the platform 24. The helical spikes 50 and 52 resemble a pair of intertwined corkscrews. According to the embodiment illustrated in FIGS. 1–6, the first and second helical spikes 50 and 52 extend around the axis 22. The spikes 50 and 52 extend in a helical pattern about the axis 22 at the same, constant radius R1. It is contemplated, however, that the first and second helical spikes 50 and 52 could extend about the axis 22 at different radiuses. Further, it is contemplated that the radius of one or both of the first and second helical spikes 50 and 52 could increase or decrease as the helical spikes extend away from the platform 24. In order for the anchor 20 to be implanted endoscopically through a typical cannula 15 (FIG. 1A), the platform 24 and the helical spikes 50 and 52 should be less than 20 mm in overall diameter. It should be understood that the anchor 20 could have an overall diameter that is greater than 20 mm for certain applications, and that the anchor could be also implanted in an open surgical procedure. However, for structural stability reasons, the overall diameter of the helical spikes 50 and 52 should remain less than or equal to the diameter of the platform 24.

In the illustrated embodiment of FIGS. 1–6, the first and second helical spikes 50 and 52 have the same axial length, and also have the same circular cross-sectional shape. It is contemplated, however, that the first and second helical spikes 50 and 52 could have different axial lengths. Further, it is contemplated that the helical spikes 50 and 52 could have a different cross-sectional shape, such as an oval shape. It also contemplated that the first and second helical spikes 50 and 52 could have different cross-sectional areas (i.e., one spike being thicker than the other spike). Finally, it is contemplated that the helical spikes 50 and 52 should have the same pitch, and that the pitch of the helical spikes would be selected based on the specific surgical application and quality of the bone in which the anchor 20 is to be implanted.

Each of the first and second helical spikes 50 and 52 can be divided into three portions: a connecting portion 54, an intermediate portion 56, and a tip portion 58. The connecting portion 54 of each of the helical spikes 50 and 52 is located at a proximal end 60 that adjoins the end surface 38 of the platform 24. The connection portion 54 may include barbs (not shown) for resisting pull-out of the helical spikes 50 and 52 from the vertebrae 12. According to one method for manufacturing the anchor 20, the connecting portion 54 of each of the helical spikes 50 and 52 is fixedly attached to the platform 24 by inserting, in a tangential direction, the proximal ends 60 of the helical spikes into openings (not shown) in the end surface 38 and welding the connecting portions 54 to the platform. The inserted proximal ends 60 of the helical spikes 50 and 52 help to reduce tensile bending stresses on the helical spikes under tensile (or pull-out) loads.

Alternatively, the helical spikes 50 and 52 may be formed integrally with the platform 24, such as by casting the anchor 20. If the anchor 20 is cast, it is contemplated that a fillet (not shown) may be added at the junction of the helical spikes 50 and 52 and the platform 24 to strengthen the junction and minimize stress concentrations at the connecting portions 54. The fillet at the junction of the helical spikes 50 and 52 and the platform 24 also helps to reduce bending stresses in the connection portions 54 of the helical spikes under tensile (or pull-out) loads.

As best seen in FIG. 6, the connecting portions 54 at the proximal ends 60 of the first and second helical spikes 50 and 52 are spaced 180° apart about the axis 22 to balance the anchor 20 and evenly distribute loads on the helical spikes. The connecting portion 54 of each of the helical spikes 50 and 52 has a first cross-sectional diameter D1 (FIG. 5).

The tip portion 58 of each of the helical spikes 50 and 52 is located at a distal end 62 of the helical spikes. The intermediate portion 56 of each of the helical spikes 50 and 52 extends between the tip portion 58 and the connecting portion 54. The intermediate portion 56 and the tip portion 58 of each of the helical spikes 50 and 52 has a second cross-sectional diameter D2 that is less than or equal to the first cross-sectional diameter D1 of the connecting portions 54. If the second cross-sectional diameter D2 is less than the first cross-sectional diameter D1, the increased thickness of the connecting portions 54 of the helical spikes 50 and 52 will help to provide the anchor 20 with increased tensile strength at the junction of the helical spikes and the platform 24.

Figure 7:
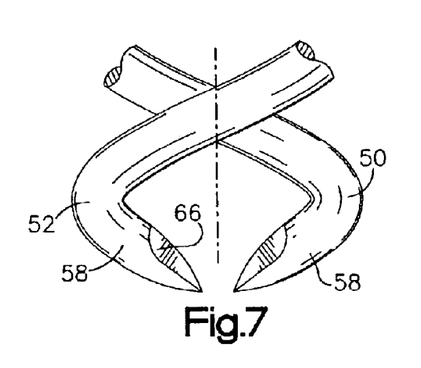
FIG. 7 illustrates an alternate configuration for an end portion of the apparatus of FIG. 1.

The tip portion 58 of each of the helical spikes 50 and 52 illustrated in FIGS. 1–6 has an elongated conical shape with a sharp pointed tip 68 for penetrating into the vertebrae 12 as the platform 24 of the anchor 20 is rotated in a clockwise direction. FIG. 7 illustrates an alternative, self-tapping configuration for the tip portions 58 which includes a planar surface 66 for driving into the vertebrae 12, in the same manner that a wood chisel turned upside-down drives into wood, as the platform 24 is rotated. It is contemplated that the tip portions 58 could also have a pyramid shape (not shown), similar to the tip of a nail.

Figure 17:
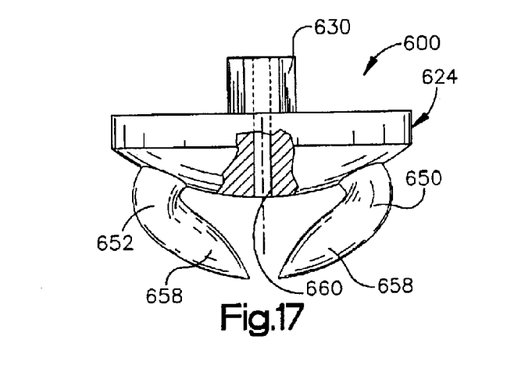
FIG. 17 is a side view of a starter tool for use with the present invention.

To implant the anchor 20, a starter tool 600 (FIG. 17) is used to punch two holes 602 and 604 (FIG. 18) in the cortical bone of the vertebrae 12. The starter tool 600 includes a platform 624 similar to the platform 24 and a plurality of helical spikes 650 and 652 similar to the helical spikes 50 and 52. The platform 624 includes a feature, such as a hexagonal drive projection 630, for drivingly rotating the starter tool 600. The spikes 650 and 652 correspond in diameter and quantity to the helical spikes 50 and 52, but are much shorter in axial length in order to increase their strength and resistance to radially outward deformation. The holes 602 and 604 are punched in locations that correspond to the spacing of the tip portions 58 of the helical spikes 50 and 52 on the anchor 20. It should be noted that one or both of the configurations of the tip portions 58 illustrated in FIGS. 1–7 may be able to punch through the cortical bone upon rotation of the anchor 20, thus eliminating the need for the starter tool 600 to punch holes in the cortical bone.

Figure 18:
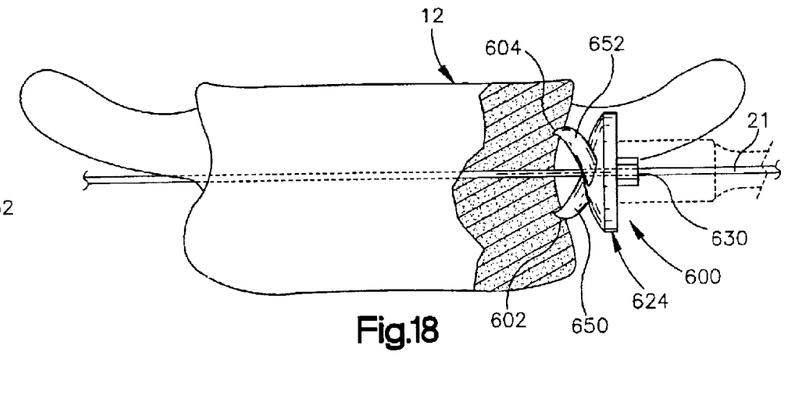
FIG. 18 is a view showing the starter tool of FIG. 17.

As shown in FIG. 18, alignment of the starter tool 600 along the desired axis through the vertebrae 12 may be ensured by threading the starter tool down over a wire 21 that has been previously passed through the vertebrae. To allow for this, the starter tool 600 may optionally include a central bore 660.

The tip portions 58 are then placed in the holes 602 and 604 in the vertebrae 12 and a rotatable driver 70 (FIG. 4) is inserted into the slot 32 in the platform 24. The driver 70 is then rotated, causing the anchor 20 to rotate as well. It is contemplated that a cylindrical sleeve 17 (FIG. 1A) may be placed around the intermediate portions 56 and the connecting portions 54 of the helical spikes 50 and 52 to prevent the helical spikes from deforming radially outward during the initial rotation of the anchor 20.

Rotation of the anchor 20 screws the helical spikes 50 and 52 into the cancellous bone of the vertebrae 12. The tangentially-oriented connection between the connecting portions 54 of the helical spikes 50 and 52 and the platform 24 minimizes bending loads on the connecting portions during rotation of the anchor 20. Further, the tangentially-oriented connection ensures that the force vector resulting from torque and axial force applied by the driver 70 to platform 24 is transmitted along the helical centerline (not shown) of each of the helical spikes 50 and 52.

As the anchor 20 is rotated, the tip portion 58 of the first helical spike 50 penetrates the cancellous bone and cuts a first helical tunnel 80 (FIG. 1) through the vertebrae 12. Simultaneously, the tip portion 58 of the second helical spike 52 penetrates the cancellous bone of the vertebrae 12 and cuts a second helical tunnel 82. The first and second helical tunnels 80 and 82 are shaped like the helical spikes 50 and 52, respectively. Continued rotation of the anchor 20 embeds the helical spikes 50 and 52 deeper into the cancellous bone of the vertebrae 12. The anchor 20 is rotated until the convex end surface 38 of the platform 24 seats against the concave side surface 14 of the vertebrae 12 as shown in FIG. 1.

Figure 2:
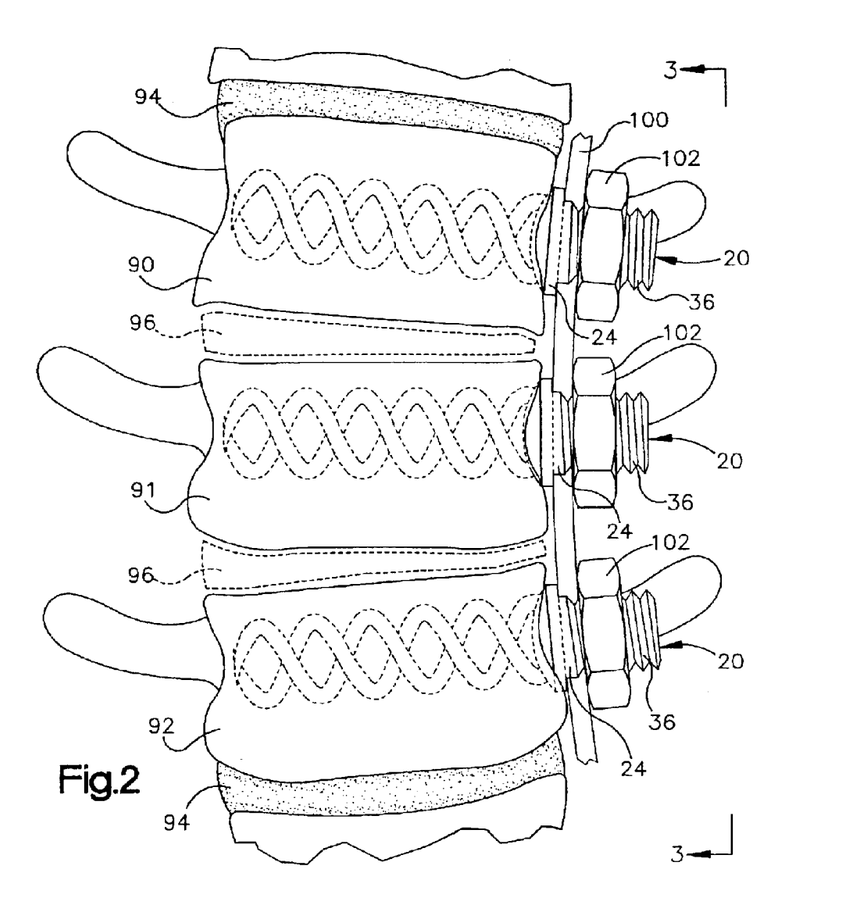
FIG. 2 is a schematic anterior view of several vertebral bodies implanted with the apparatus of FIG. 1 and connected by a spinal fixation implant in accordance with the present invention.
Figure 3:
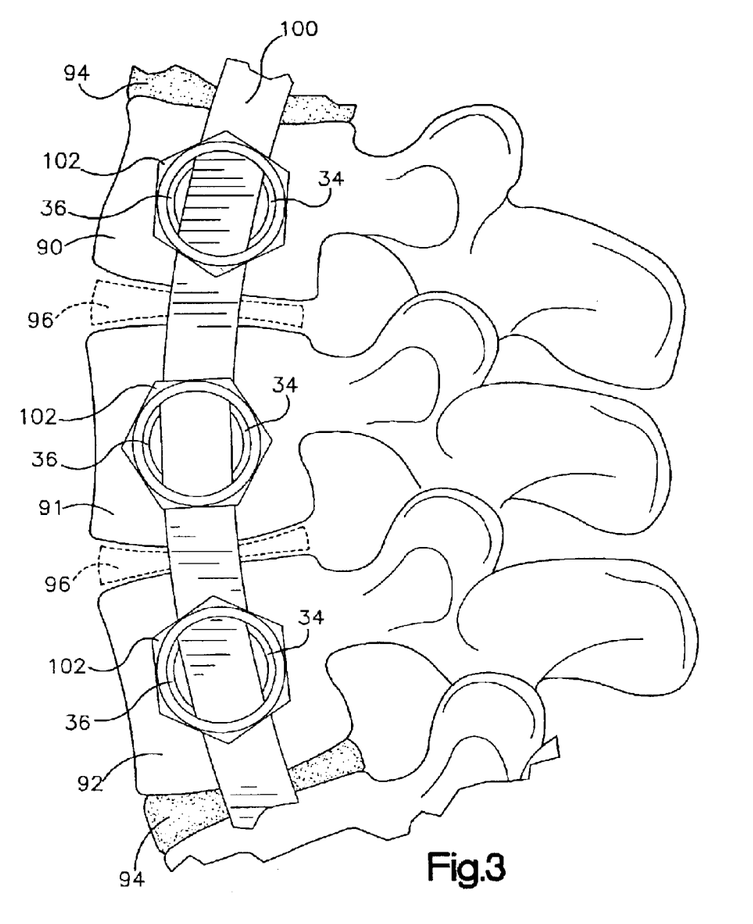
FIG. 3 is a side view taken along line 3—3 in FIG. 2.

FIGS. 2 and 3 illustrate how the anchor 20 is used for segmental spinal fixation of lumbar vertebrae to treat a patient with scoliosis. Lumbar vertebrae L3–L5, indicated by reference numbers 90, 91, and 92, respectively, are shown in FIGS. 2 and 3. Normally, disk material 94 separates each of the lumbar vertebrae 90–92. However, in order to correct the scoliosis, the surgeon removes the disk material 94 between the vertebrae 90–92. The spaces left between the vertebrae 90–92 are subsequently filled with bone graft material 96 (shown schematically in FIGS. 2 and 3) that fuses the vertebrae together over time. Spinal fixation instrumentation, such as a rod or a beam 100, is used to support the vertebrae 90–92 until the vertebrae fuse together.

As shown in FIGS. 2 and 3, the vertebrae 90–92 are each implanted with the anchor 20 according to the present invention as described above. The beam 100, which is bent into a desired shape by the surgeon, is placed into the slot 32 in each of the anchors 20. A nut 102 is then screwed onto the threads 34 and 36 on each of the platforms 24 and is tightened to secure the beam 100 to each of the anchors 20.

When implanted, the anchors 20 are subjected to substantial forces caused by human body movement and muscle memory. In some cases, these forces can tend to pull the known screws used in such an application out of the vertebrae 90–92 or can cause the screws to toggle in the vertebrae. However, when the helical spike 50 and 52 are embedded in the vertebrae 90–92, the two helical spikes of the anchors 20 provide the anchors with a high resistance to pull-out forces. Preliminary cadaver testing indicates that the anchor 20 is so resistant to being pulled axially from a vertebral body that the vertebral body itself is likely to fail before the anchor pulls out under high tensile load. Further, the helical spikes 50 and 52, and their tangential connection with the platform 24, provide the anchors 20 with a high resistance to toggling in the vertebrae 90–92.

Figure 8:
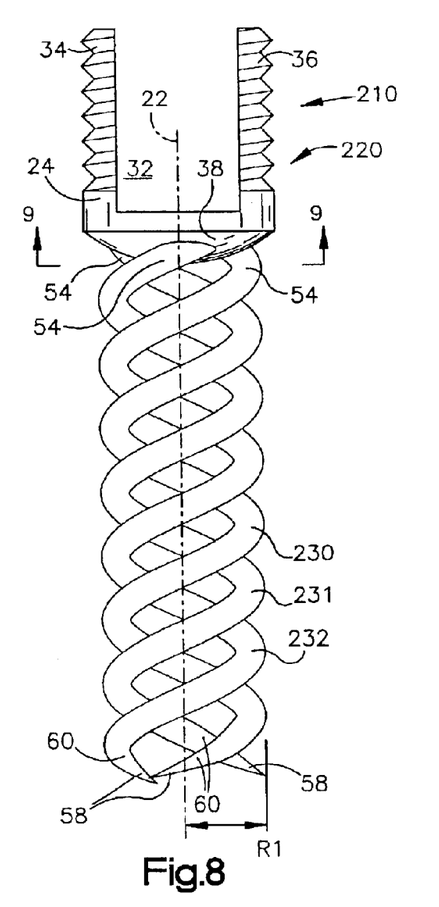
FIG. 8 is a side view illustrating a second embodiment of an apparatus in accordance with the present invention.
Figure 9:
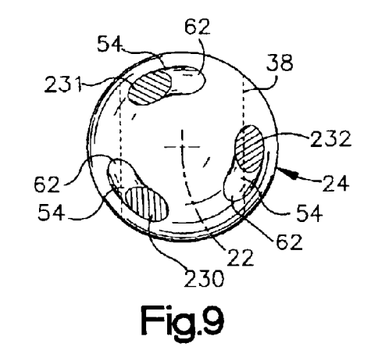
FIG. 9 is a sectional view taken along line 9—9 in FIG. 8.

FIGS. 8 and 9 illustrate an apparatus 210 constructed in accordance with a second embodiment of the present invention. In the second embodiment of FIGS. 8 and 9, reference numbers that are the same as those used in the first embodiment of FIGS. 1–6 designate parts that are the same as parts in the first embodiment.

According to the second embodiment, the apparatus 210 comprises an anchor 220 having three helical spikes 230, 231, and 232 projecting tangentially from the end surface 38 of the platform 24. The spikes 230–232 extend around the axis 22. As shown in FIG. 9, the connecting portions 54 at the proximal ends 60 of the helical spikes 230–232 are spaced 120° apart about the axis 22, which balances the anchor 220 and evenly distributes loads on the helical spikes. As in the first embodiment of FIGS. 1–6, in the second embodiment of FIGS. 8 and 9, the cross-sectional diameter of the connecting portions 54 of the helical spikes 230–232 is greater than or equal to the cross-sectional diameter of the intermediate portions 56 and the tip portions 58 of the helical spikes.

Each of the three helical spikes 230–232 extends in a helical pattern about the axis 22 at the same, constant radius R1. It is contemplated, however, that one or more of the helical spikes 230–232 could extend about the axis 22 at different radiuses. Further, it is contemplated that the radius of one or more helical spikes 230–232 could increase or decrease as the helical spikes extend away from the platform 24.

As shown in FIG. 8, the three helical spikes 230–232 have the same axial length and also have the same circular cross-sectional shape. It is contemplated, however, that one or more of the helical spikes 230–232 could have different axial lengths. Further, it is contemplated that one or more of the helical spikes 230–232 could have a different cross-sectional shape, such as an oval shape. It also contemplated that the one or more of the helical spikes 230–232 could have different cross-sectional areas (i.e., one spike being thicker or thinner than the other two spikes). Finally, it is contemplated that the helical spikes 230–232 should have the same pitch, and that the pitch of the helical spikes would be selected based on the specific surgical application and quality of the bone in which the anchor 20 is to be implanted.

The tip portion 58 of each of the helical spikes 230–232 illustrated in FIG. 8 has an elongated conical shape for penetrating into a vertebrae as the platform 24 of the anchor 220 is rotated in the clockwise direction. It should be understood that the tip portions 58 of the helical spikes 230–232 of the anchor 220 could alternatively be configured like the tip portions illustrated in FIG. 7.

The anchor 220 according to the second embodiment of FIGS. 8 and 9 is implanted in a vertebrae in the same manner as the anchor 20 according to the first embodiment. Further, the anchor 220 according to the second embodiment may also be used to mount spinal fixation instrumentation in same manner as the anchor 20 according to the first embodiment. The anchor 220 according to the second embodiment, when implanted in a vertebrae, is highly resistant to being pulled out of the vertebrae and to toggling in the vertebrae despite being subjected to substantial forces caused by human body movement and muscle memory.

Figure 10:
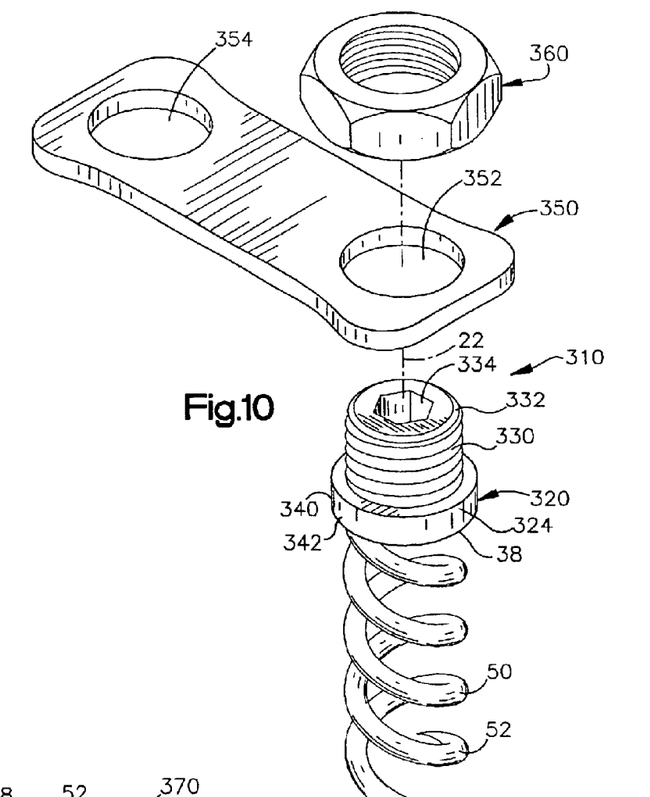
FIG. 10 is an exploded perspective view illustrating a third embodiment of an apparatus in accordance with the present invention.
Figure 11:
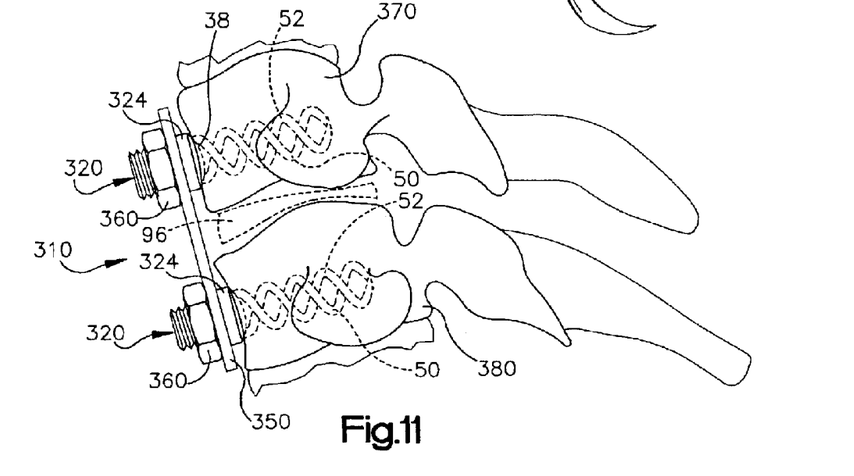
FIG. 11 is a schematic side view of the apparatus of FIG. 10 implanted in a pair of vertebral bodies.

FIGS. 10 and 11 illustrate an apparatus 310 constructed in accordance with a third embodiment of the present invention. In the third embodiment of FIGS. 10 and 11, reference numbers that are the same as those used in the first embodiment of FIGS. 1–6 designate parts that are the same as parts in the first embodiment.

According to the third embodiment, the apparatus 310 comprises an anchor 320 having a platform 324. The platform 324 has a threaded outer surface 330 adjacent a first end portion 332 and a cylindrical outer surface 340 adjacent a second end portion 342. The first end portion 332 of the platform 324 further includes an axial recess 334. The recess 334 has a hexagonal configuration for receiving a tool (not shown) for drivingly rotating the anchor 320. The first and second helical spikes 50 and 52 project from the end surface 38 of the platform 324.

The apparatus 310 further includes a plate 350 and a nut 360. The plate 350 has a first opening 352 for receiving the portion of the platform 324 which has the threaded outer surface 330. The plate 350 has a second opening 354 for receiving a second anchor 320 (see FIG. 11) or other fixation instrumentation (not shown). When the anchor 320 is implanted in a vertebrae, the nut 360 screws onto the threaded outer surface 330 of the platform 324 to secure the plate 350 to the anchor 320.

The anchor 320 according to the third embodiment of FIGS. 10 and 11 is implanted in a vertebrae in the same manner as the anchor 20 according to the first embodiment. FIG. 11 shows a pair of the anchors 320 implanted in two cervical vertebrae 370 and 380. The end surface 38 of each of the anchors 320 engages a respective anterior surface on each of the vertebrae 370 and 380. The plate 350 connects the anchors 320 to help support the vertebrae 370 and 380 and transfer loads between the vertebrae until the bone graft material 96 fuses the vertebrae. Like the anchor 20 according to the first embodiment, the anchor 320 according to the third embodiment, when implanted in the vertebrae, is highly resistant to being pulled out of the vertebrae and to toggling in the vertebrae despite being subjected to substantial forces caused by human body movement and muscle memory.

Figure 12:
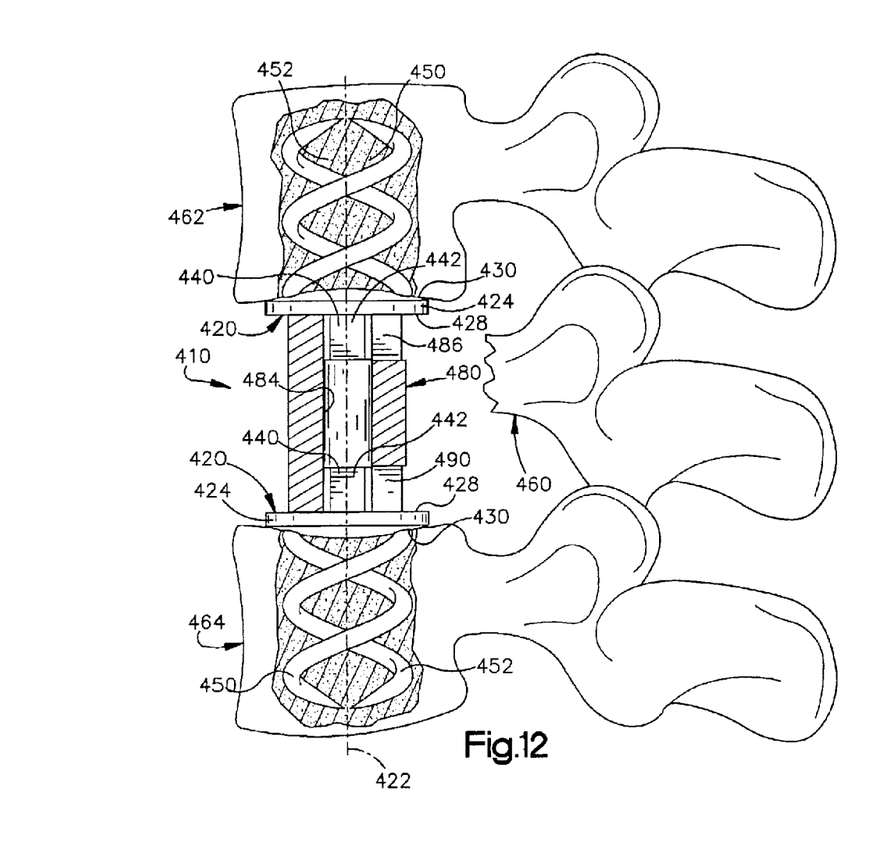
FIG. 12 is a schematic view, partially in section, of a fourth embodiment of the present invention.
Figure 13:
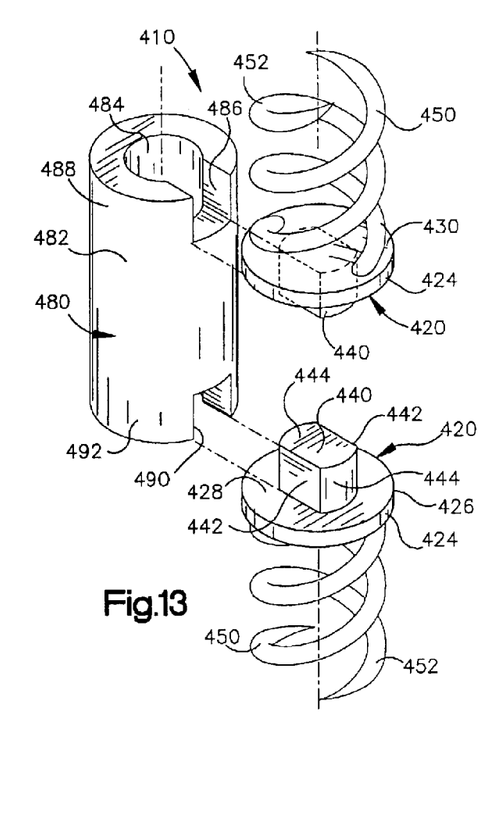
FIG. 13 is an exploded perspective view of the apparatus of FIG. 12.

FIGS. 12 and 13 illustrate an apparatus 410 constructed in accordance with a fourth embodiment of the present invention. In the fourth embodiment of FIGS. 12 and 13, reference numbers that are the same as those used in the first embodiment of FIGS. 1–6 designate parts that are the same as parts in the first embodiment.

According to the fourth embodiment, the apparatus 410 comprises a pair of anchors 420 extending around a longitudinal axis 422. Each of the anchors 420 includes a platform 424 that is substantially wider than the platform 24 of the anchor 20 in the first embodiment. The platform 424 has a cylindrical outer surface 426 that extends between oppositely disposed first and second end surfaces 428 and 430. An attachment tab 440 projects axially away from the first end surface 428 of the platform 424. The attachment tab 440 includes a pair of oppositely disposed planar surfaces 442 and a pair of oppositely disposed arcuate surfaces 444.

The attachment tabs 440 provide structure for connecting spinal fixation instrumentation to each of the platforms 424 and for driving the anchors 420. The second end surface 430 of the platform 424 of each anchor 420 has a shape that is complimentary to the shape of an upper or lower surface of a vertebrae. Similar to the first embodiment of FIGS. 1–6, the anchors 420 have first and second helical spikes 450 and 452 that project from the second end surface 430 of the platform 424. The helical spikes 450 and 452 extend along the axis 422, but are significantly larger in diameter than the helical spikes 50 and 52 in the first embodiment. It should be understood that the anchors 420 could alternatively have three helical spikes as shown in the second embodiment of FIGS. 8 and 9.

The apparatus 410 according to the fourth embodiment of FIGS. 12 and 13 is particularly useful for a corpectomy application in which a damaged vertebrae is removed. As is shown in FIG. 12, after a portion of a damaged vertebrae 460 is removed, a first one of the pair of anchors 420 is implanted into a vertebrae 462 directly above the removed vertebrae 460 and a second one of the pair of anchors 420 is implanted into a vertebrae 464 directly below the removed vertebrae.

The anchors 420 are implanted in the vertebrae 462 and 464 in much the same manner as the anchor 20 according to the first embodiment. A rotatable tool (not shown) engages the planar surfaces 442 on the attachment tab 440 and rotates each of the anchors 420 to screw the helical spikes 450 and 452 of each of the anchors into the respective vertebrae 462 and 464. The anchors 420 are implanted so that they extend co-linearly along the axis 422. When implanted, the helical spikes 450 and 452 of the anchor 420 in the vertebrae 462 extend in an upward direction from the platform 430 of the upper (as viewed in the Figures) anchor, while the helical spikes 450 and 452 of the other anchor in the vertebrae 464 extend in a downward direction from the platform 430 of the lower (as viewed in the Figures) anchor.

A spinal fixation implant in the form of a cylinder member 480 connects the pair of anchors 420 to structurally support the vertebral column in the absence of the removed vertebrae 460. The cylinder member 480 has a cylindrical outer surface 482 and an eccentric inner surface 484. The cylinder member 480 has a first slot 486 at a first end 488 and a second slot 490 at a second end 492. The first and second slots 486 and 490 receive the attachment tabs 440 on the anchors 420 and allow the cylinder member 480 to be inserted between the anchors. Once inserted between the anchors 420, the cylinder member 480 is then rotated relative to the anchors about the axis 422. Rotation of the cylinder member 480 brings the arcuate surfaces 444 on the attachment tabs 440 of the anchors 420 into frictional engagement with the eccentric inner surface 484 of the cylinder member, thereby securing the cylinder member.

As with the previous embodiments, the anchors 420 according to the fourth embodiment, when implanted, are highly resistant to being pulled out of the vertebrae 462 and 464 and to toggling in the vertebrae despite being subjected to substantial forces caused by human body movement and muscle memory.

Figure 12A:
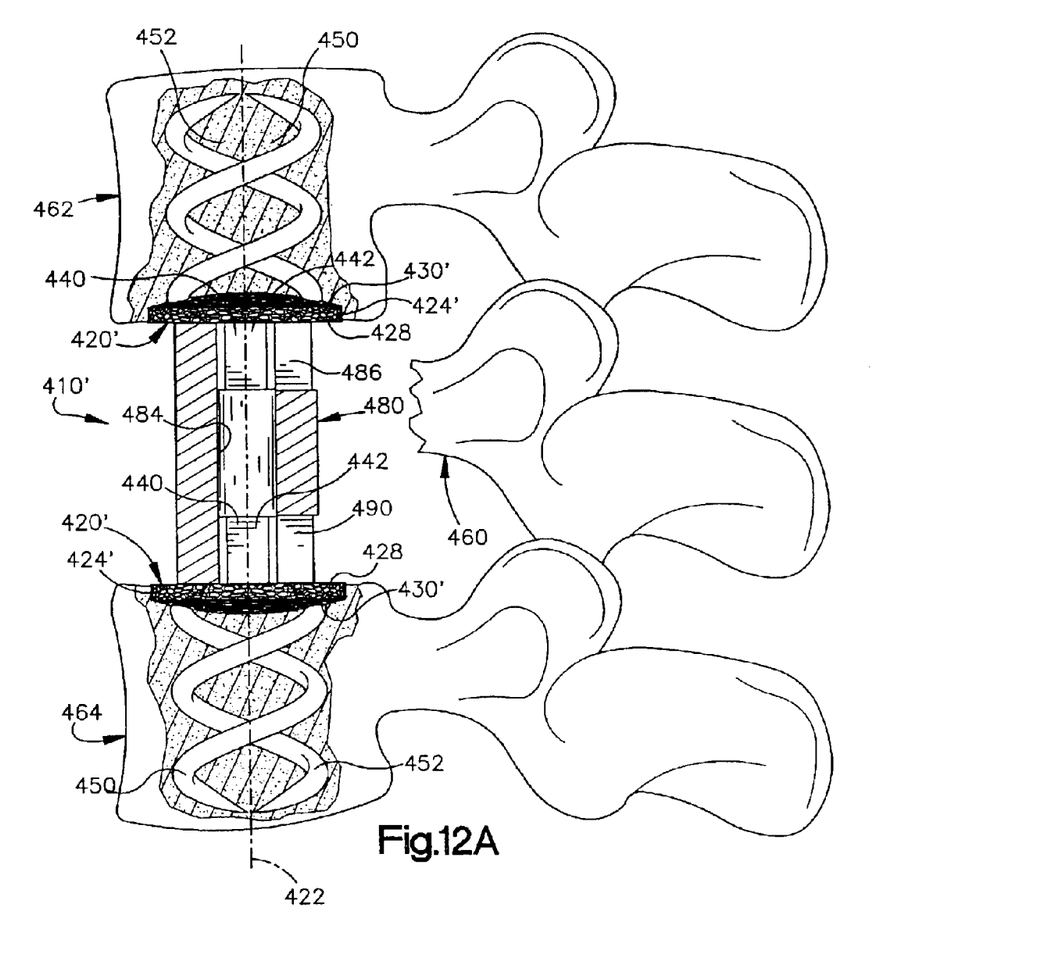
FIG. 12A is a view similar to FIG. 12 illustrating an alternate implantation of the apparatus of FIG. 12.

FIG. 12A illustrates an alternate implantation of the apparatus 410 of FIG. 12. In FIG. 12A, an apparatus 410' comprises a pair of anchors 420' that are identical to the anchors 420 described above, except that they include a platform 424' that has a porous surface 430', as has been previously described. The porous surface 430' has an increased surface area that promotes bone in-growth. In all other respects, the apparatus 410' is identical to the apparatus 410 described above.

The apparatus 410' is implanted in the vertebrae 462 and 464 in the same manner as described above, except that the platforms 424' on the anchors 420' are recessed into the end surfaces of the two vertebrae, as may be seen in FIG. 12A. The porous surfaces 430' on the platforms 424' help with long term fixation of the anchors 420' to the vertebrae 462 and 464.

Figure 14:
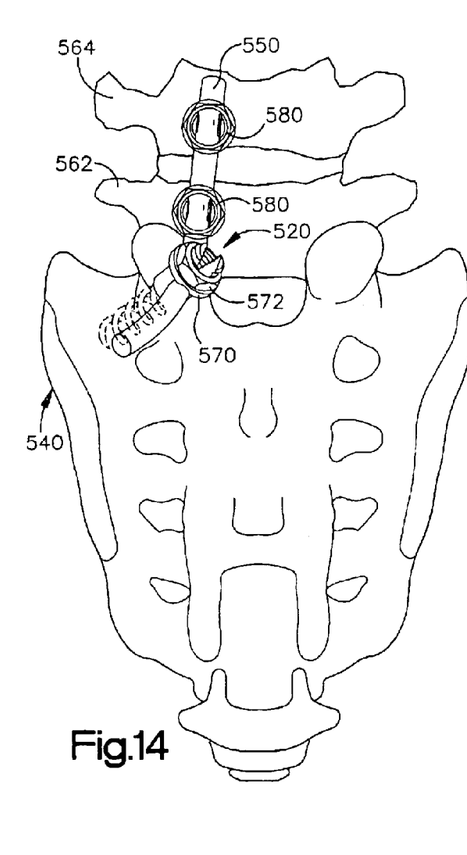
FIG. 14 is a schematic posterior view illustrating a fifth embodiment of the present invention.
Figure 15:
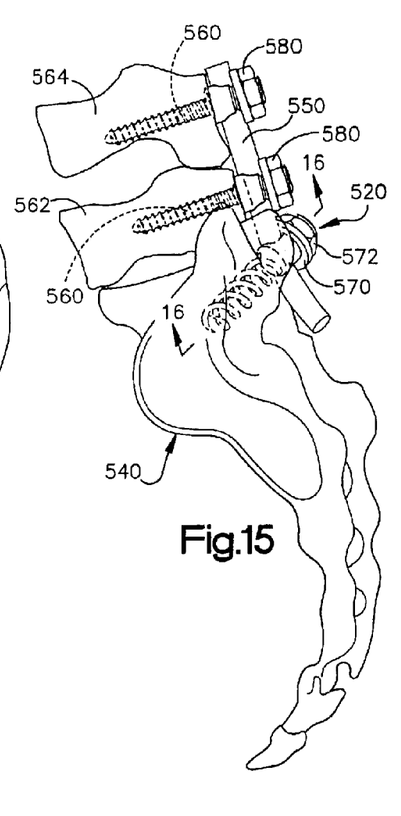
FIG. 15 is a side view of FIG. 14.
Figure 16:
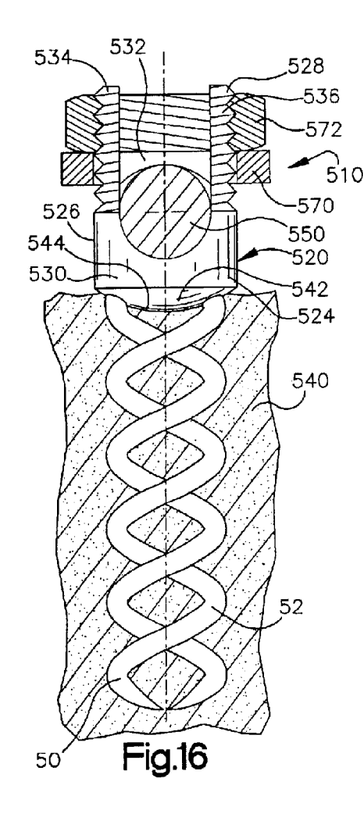
FIG. 16 is a sectional view taken along line 16—16 in FIG. 15.

FIGS. 14–16 illustrate an apparatus 510 constructed in accordance with a fifth embodiment of the present invention. In the fifth embodiment of FIGS. 14–16, reference numbers that are the same as those used in the first embodiment of FIGS. 1–6 designate parts that are the same as parts in the first embodiment.

According to the fifth embodiment, the apparatus 510 comprises an anchor 520 implanted into a sacrum 540. The anchor 520 includes a platform 524 having a generally cylindrical outer surface 526 extending between oppositely disposed first and second ends 528 and 530. The platform 524 includes a slot 532 that extends axially from the first end 528 toward the second end 530 of the platform. Adjacent the first end 528, the outer surface of the platform 524 includes first and second segments of external threads 534 and 536 that are separated by the slot 532. The slot 532 and the threads 534 and 536 on the platform 524 provide structure for connecting a rod 550 to the anchor 520.

The second end 530 of the platform 524 includes an end surface 542 having a shape that is a complimentary to the shape of a surface 544 (FIG. 16) of the sacrum 540. The anchor 520 includes the first and second helical spikes 50 and 52 that extend from the end surface 542 of the platform 524.

The anchor 520 according to the fifth embodiment of FIGS. 14–16 is implanted in the sacrum 540 in much the same manner as the anchor 20 according to the first embodiment is implanted in the vertebrae 12. As shown in FIG. 15, in addition to the anchor 520 being implanted in the sacrum 540, known screws 560 are implanted in the pedicles of lumbar vertebrae 562 and 564 above the sacrum. The rod 550 is then bent into a desired shape by the surgeon and placed into the slot 532 in the platform 524 of the anchor 520. A seat 570 is placed over the first end 528 of the platform 524 and engages the rod 550. A nut 572 screws down over the seat 570 and clamps the rod 550 to the anchor 520. In a similar fashion, the nuts 580 secure the rod 550 to the screws 560 implanted in the vertebrae 562 and 564 above the sacrum 540.

As in the first embodiment, the anchor 520 according to the fifth embodiment, when implanted, is highly resistant to being pulled out of the sacrum 540 and to toggling in the sacrum despite being subjected to substantial forces caused by human body movement and muscle memory.

Figure 16A:
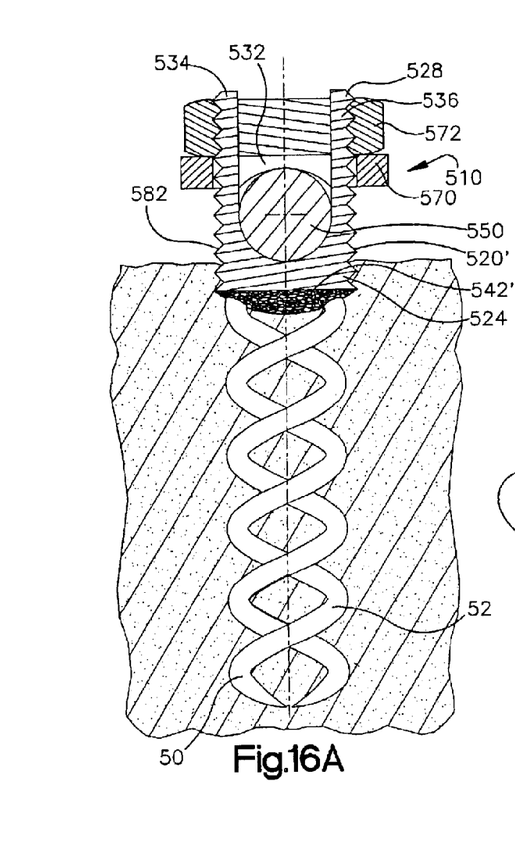
FIG. 16A is a view similar to FIG. 16 illustrating an alternate configuration.

FIG. 16A illustrates an alternate construction for an anchor 520' in which the surface 542' has a porous texture, such as has been previously described in connection with FIG. 6A. Further, the platform 524 on the anchor 520' includes a cylindrical outer surface 580 that extends parallel to the axis of the anchor and has external threads 582 for screwing into the bone. The anchor 520' is thus designed to be recessed into the bone as shown in FIG. 16A to help with fixation as the bone in-growth occurs.

From the above description of the invention, those skilled in the art will perceive improvements, changes and modifications. It should be understood that the present invention can be used for a variety of purposes and implanted in other bones besides bones in the vertebral column. Further, it should be understood that more than one of the apparatuses disclosed herein may be implanted into a single bone, such as a vertebral body. Such improvements, changes and modifications within the skill of the art are intended to be covered by the appended claims.

Having described the invention, I claim:

1. An anchor which is implantable into a bone in a patient's body and, when implanted, is resistant to toggling in the bone and to being pulled from the bone, said anchor comprising:

a head end portion having a surface that extends transverse to a central axis of said anchor and is engageable with the bone; and a plurality of helical spikes extending from said surface on said head end portion of said anchor and are engageable with the bone, each of said plurality of helical spikes having a helical central axis that forms a helix around said central axis of said anchor, each of said plurality of helical spikes further having a circular cross-sectional configuration as viewed in a plane extending perpendicular to said helical central axis of each of said helical spikes and having a distal end portion with a tip that penetrates the bone as said head end portion is rotated relative to the bone;

each helical spike of said plurality of helical spikes being formed separately from said head end portion of said anchor and having a proximal end portion which extends through said surface on said head end portion of said anchor into an opening in said head end portion of said anchor.

2. An anchor as set forth in claim 1 wherein said proximal end portion of each helical spike extends at an acute angle to said surface on said head end portion of said anchor.

3. An anchor as set forth in claim 1 wherein said surface on said head end portion of said anchor has a convex configuration and has a center of curvature which is offset from said surface on said head end portion of said anchor in a direction away from said distal end portion of each of said plurality of helical spikes.

4. An anchor as set forth in claim 1 wherein each of said helical spikes has a circular cross-sectional configuration with the same diameter throughout the extent of each of said helical spikes between a proximal end portion of each of said helical spikes and said distal end portion of each of said helical spikes.

5. An anchor as set forth in claim 1 wherein said plurality of helical spikes includes at least two helical spikes.

6. An anchor as set forth in claim 1 wherein said plurality of helical spikes includes at least three helical spikes.

7. An anchor as set forth in claim 1 wherein said surface on said head end portion is circular and is disposed in a coaxial relationship with said central axis of said anchor and has a diameter which is greater than an outside diameter of said helical spikes.

8. An anchor as set forth in claim 1 wherein said surface on said head end portion has a rough, porous texture that provides an increased surface area for said surface to promote bone in-growth.

9. An anchor which is implantable into a bone in a patient's body and, when implanted, is resistant to toggling in the bone and to being pulled from the bone, said anchor comprising:

a head end portion having a surface that extends transverse to a central axis of said anchor and is engageable with the bone; and a plurality of helical spikes extending from said surface on said head end portion of said anchor and are engageable with the bone, each of said plurality of helical spikes having a helical central axis that forms a helix around said central axis of said anchor, each of said plurality of helical spikes further having a circular cross-sectional configuration as viewed in a plane extending perpendicular to said helical central axis of each of said helical spikes and having a distal end portion with a tip that penetrates the bone as said head end portion is rotated relative to the bone;

said head end portion including means for connection with a spinal fixation implant.

10. An apparatus comprising:

at least one anchor which is implantable into a bone in a patient's body and, when implanted, is resistant to toggling in the bone and to being pulled from the bone; and a fixation implant for extending between and connecting a plurality of bones;

said at least one anchor including a head end portion having a surface that extends transverse to a central axis of said anchor and is engageable with the bone, said head end portion having means for connecting with said fixation implant;

said head end portion of said at least one anchor having a plurality of helical spikes that extend from said surface and which extend transverse to a central axis of said at least one anchor and are engageable with the bone, each of said plurality of helical spikes having a helical central axis that forms a helix around said central axis of said at least one anchor;

each helical spike of said plurality of helical spikes further having a distal end portion with a tip which penetrates the bone as said at least one anchor is rotated relative to the bone and a circular cross-sectional configuration as viewed in a plane extending perpendicular to said helical central axis of each of said helical spikes throughout a length of each of said helical spikes extending from a proximal end portion to said distal end portion of each of said one helical spikes;

said proximal end portion of each of said plurality of helical spikes extending at an acute angle to said surface on said head end portion of said at least one anchor.

11. An apparatus as set forth in claim 10 wherein said plurality of helical spikes includes at least two helical spikes.

12. An apparatus as set forth in claim 10 wherein said plurality of helical spikes includes at least three helical spikes.

13. An apparatus as set forth in claim 10 wherein said at least one anchor comprises a first anchor for implantation into a first bone and a second anchor for implantation into a second bone.

14. An apparatus comprising:

at least one anchor which is implantable into a bone in a patient's body and, when implanted, is resistant to toggling in the bone and to being pulled from the bone; and a fixation implant for extending between and connecting a plurality of bones;

said at least one anchor including a head end portion having a surface that extends transverse to a central axis of said anchor and is engageable with the bone, said head end portion having means for connecting with said fixation implant;

said head end portion of said at least one anchor having a plurality of helical spikes that extend from said surface and which extend transverse to a central axis of said at least one anchor and are engageable with the bone, each of said plurality of helical spikes having a helical central axis that forms a helix around said central axis of said at least one anchor;

each helical spike of said plurality of helical spikes further having a distal end portion with a tip which penetrates the bone as said at least one anchor is rotated relative to the bone and a circular cross-sectional configuration as viewed in a plane extending perpendicular to said helical central axis of each of said helical spikes throughout a length of each of said helical spikes extending from a proximal end portion to said distal end portion of each of said helical spikes;

said surface on said head end portion of said at least one anchor having a convex configuration and having a center of curvature which is offset from said surface on said head end portion in a direction away from said distal end portion of each of said plurality of helical spikes.

15. An apparatus comprising:

at least one anchor which is implantable into a bone in a patient's body and, when implanted, is resistant to toggling in the bone and to being pulled from the bone; and a fixation implant for extending between and connecting a plurality of bones;

said at least one anchor including a head end portion having a surface that extends transverse to a central axis of said anchor and is engageable with the bone, said head end portion having means for connecting with said fixation implant;

said head end portion of said at least one anchor having a plurality of helical spikes that extend from said surface and which extend transverse to a central axis of said at least one anchor and are engageable with the bone, each of said plurality of helical spikes having a helical central axis that forms a helix around said central axis of said at least one anchor;

each helical spike of said plurality of helical spikes further having a distal end portion with a tip which penetrates the bone as said at least one anchor is rotated relative to the bone and a circular cross-sectional configuration as viewed in a plane extending perpendicular to said helical central axis of each of said helical spikes throughout a length of each of said helical spikes extending from a proximal end portion to said distal end portion of each of said helical spikes;

said surface on said head end portion being circular and being disposed in a coaxial relationship with said central axis of said at least one anchor, said head end portion having a diameter which is greater than an outside diameter of said plurality of helical spikes.

16. An apparatus comprising:

at least one anchor which is implantable into a bone in a patient's body and, when implanted, is resistant to toggling in the bone and to being pulled from the bone; and a fixation implant for extending between and connecting a plurality of bones;

said at least one anchor including a head end portion having a surface that extends transverse to a central axis of said anchor and is engageable with the bone, said head end portion having means for connecting with said fixation implant;

said head end portion of said at least one anchor having a plurality of helical spikes that extend from said surface and which extend transverse to a central axis of said at least one anchor and are engageable with the bone, each of said plurality of helical spikes having a helical central axis that forms a helix around said central axis of said at least one anchor;

each helical spike of said plurality of helical spikes further having a distal end portion with a tip which penetrates the bone as said at least one anchor is rotated relative to the bone and a circular cross-sectional configuration as viewed in a plane extending perpendicular to said helical central axis of each of said helical spikes throughout a length of each of said helical spikes extending from a proximal end portion to said distal end portion of each of said helical spikes;

said surface on said head end portion having a rough, porous texture that provides an increased surface area to promote bone in-growth.

17. An apparatus comprising:

at least one anchor which is implantable into a bone in a patient's body and, when implanted, is resistant to toggling in the bone and to being pulled from the bone; and a fixation implant for extending between and connecting a plurality of bones;

said at least one anchor including a head end portion having a surface that extends transverse to a central axis of said anchor and is engageable with the bone, said head end portion having means for connecting with said fixation implant;

said head end portion of said at least one anchor having a plurality of helical spikes that extend from said surface and which extend transverse to a central axis of said at least one anchor and are engageable with the bone, each of said plurality of helical spikes having a helical central axis that forms a helix around said central axis of said at least one anchor;

each helical spike of said plurality of helical spikes further having a distal end portion with a tip which penetrates the bone as said at least one anchor is rotated relative to the bone and a circular cross-sectional configuration as viewed in a plane extending perpendicular to said helical central axis of each of said helical spikes throughout a length of each of said helical spikes extending from a proximal end portion to said distal end portion of each of said helical spikes; and an anchor starter for forming starting holes in the bone that said plurality of helical spikes are received in, said anchor starter comprising a platform having a surface that extends transverse to a longitudinal axis of said anchor starter and a plurality of helical spikes extending from said surface, said plurality of helical spikes on said anchor starter corresponding in quantity and size to said plurality of helical spikes on said anchor but are substantially shorter in axial length to resist radially outward deformation during rotation of said platform.

* * * * *